United States Patent
Dahmane et al.

(10) Patent No.: US 8,669,243 B2
(45) Date of Patent: Mar. 11, 2014

(54) STEROID-DERIVED CYCLOPAMINE ANALOGS AND METHODS FOR USING THE SAME IN THE PREVENTION OR TREATMENT OF CANCER

(75) Inventors: Nadia Dahmane, Philadelphia, PA (US); Jeffrey D. Winkler, Wynnewood, PA (US)

(73) Assignees: The Wistar Institute, Philadelphia, PA (US); The Trustees of the University of Pennsylvania, Philadelphia, PA (US)

(*) Notice: Subject to any disclaimer, the term of this patent is extended or adjusted under 35 U.S.C. 154(b) by 162 days.

(21) Appl. No.: 13/160,702

(22) Filed: Jun. 15, 2011

(65) Prior Publication Data

US 2011/0306662 A1 Dec. 15, 2011

Related U.S. Application Data

(63) Continuation-in-part of application No. 12/739,991, filed as application No. PCT/US2008/081704 on Oct. 30, 2008, now Pat. No. 8,575,141.

(60) Provisional application No. 61/018,763, filed on Jan. 3, 2008, provisional application No. 60/983,680, filed on Oct. 30, 2007.

(51) Int. Cl.
*A61K 31/58* (2006.01)
*C07D 307/94* (2006.01)

(52) U.S. Cl.
USPC ............................ 514/173; 549/456

(58) Field of Classification Search
None
See application file for complete search history.

(56) References Cited

U.S. PATENT DOCUMENTS

| | | | |
|---|---|---|---|
| 3,939,155 A * | 2/1976 | Brown | |
| 6,291,516 B1 | 9/2001 | Dudek et al. | 514/455 |
| 6,432,970 B2 | 8/2002 | Beachy et al. | 514/278 |
| 6,552,016 B1 | 4/2003 | Baxter et al. | 514/218 |
| 6,686,388 B2 | 2/2004 | Dudek et al. | 514/455 |
| 7,230,004 B2 | 6/2007 | Adams et al. | 514/278 |
| 2004/0060568 A1 | 4/2004 | Dudek et al. | 128/898 |
| 2004/0110663 A1 | 6/2004 | Dudek et al. | 514/2 |
| 2004/0127474 A1 | 7/2004 | Dudek et al. | 514/169 |
| 2006/0020020 A1 | 1/2006 | Dudek et al. | 514/455 |
| 2006/0074030 A1 | 4/2006 | Adams et al. | 514/23 |

FOREIGN PATENT DOCUMENTS

| | | | |
|---|---|---|---|
| WO | WO 97/08188 | * | 3/1997 |
| WO | WO 2004/026304 A1 | * | 4/2004 |
| WO | WO 2005/077968 A2 | * | 8/2005 |
| WO | WO 2006/128097 A1 | | 11/2006 |

OTHER PUBLICATIONS

Sathya et al., Endocrinology, 2002, vol. 143(8), pp. 3071-3082.*
Anderson et al. "The Selective Reaction of Aryl Halides with KOH: Synthesis of Phenols, Aromatic Ethers, and Benzofurans" Journal of the American Chemical Society 2006 vol. 128 (33): 10694-10695.
Chen et al. "Small Molecule Modulation of Smoothened Activity" PNAS 2002 vol. 99 (22): 14071-14076.
Clement et al. "HEDGEHOG-GLI1 Signaling Regulates Human Glioma Growth, Cancer Stem Cell Self-Renewal, and Tumorigenicity" Current Biology 2007 vol. 17: 165-172.
Frank-Kamenetsky et al. "Small-molecule Modulators of Hedgehog Signaling: Identification and Characterization of Smoothened Agonists and Antagonists" Journal of Biology 2002 vol. 1 (2): 10.1-10.18.
Hartwig, J. F. "Discovery and Understanding of Transition-Metal-Catalyzed Aromatic Substitution Reactions" Synlett 2006 vol. 9: 1283-1294.
Houminer, Y. and Williams, D. L. "The Solution Thermolysis of 2-, 3-, and 4-(2-Hydroxy-2-arylethyl) Pyridines" The Journal of Organic Chemistry 1983 vol. 48 (15): 2622-2625.
Liu et al. "Hedgehog Signaling and Bmi-1 Regulate Self-renewal of Normal and Malignant Human Mammary Stem Cells" Cancer Research 2006 vol. 66 (12): 6063-6071.
Mangion, I. "Buchwald-Hartwig Chemistry" Presentation Jul. 30, 2002 MacMillan Group Meeting.
Sicklick et al. "Dysregulation of the Hedgehog Pathway in Human Hepatocarcinogenesis" Carcinogenesis 2006 vol. 27 (4): 748-757.
Stecca et al. "Melanomas Require HEDGEHOG-GLI Signaling Regulated by Interactions Between GLI1 and the RAS-MEK/AKT Pathways" PNAS 2007 vol. 104 (14): 5895-5900.
Taipale et al. "Effects of Oncogenic Mutations in *Smoothened* and *Patched* Can Be Reversed by Cyclopamine" Nature 2000 vol. 406: 1005-1009.
VanRheenen, V. and Shephard, K. P. "New Synthesis of Cortico Steroids from 17-Keto Steroids: Application and Stereochemical Study of the Unsaturated Sulfoxide-Sulfenate" The Journal of Organic Chemistry 1979 vol. 44 (9): 1582-1584.

* cited by examiner

*Primary Examiner* — Savitha Rao
*Assistant Examiner* — Gregg Polansky
(74) *Attorney, Agent, or Firm* — Licata & Tyrrell P.C.

(57) ABSTRACT

The present invention relates to steroid-derived cyclopamine analogs and methods for using the same for inhibiting sonic hedgehog signaling and preventing or treating cancer. A method for synthesizing the analogs of the present invention from a steroid is also provided.

6 Claims, 4 Drawing Sheets

STEROID-DERIVED CYCLOPAMINE ANALOGS AND METHODS FOR USING THE SAME IN THE PREVENTION OR TREATMENT OF CANCER

This application is a continuation-in-part application of U.S. Ser. No. 12/739,991, filed Aug. 3, 2010 now U.S. Pat. No. 8,575,141, which is the U.S. national phase of PCT Application No. PCT/US2008/081704, filed Oct. 30, 2008, which claims benefit of U.S. Provisional Patent Application Nos. 61/018,763, filed Jan. 3, 2008 and 60/983,680, filed Oct. 30, 2007, the contents of which are incorporated herein by reference in their entireties.

BACKGROUND OF THE INVENTION

Breast cancer is the most common cancer among women, other than skin cancer. It is the second leading cause of cancer death in women, after lung cancer. Almost 180,000 women in the United States will be diagnosed with invasive breast cancer in 2007 and over 40,000 women will die from the disease in a year. It has been suggested that the failure of existing therapies may be due to the presence of a subpopulation of cells in the bulk of the tumor that are resistant to radiotherapy and chemotherapy. These cells, called breast cancer stem cells, have self-renewal and multi-pluripotency characteristics. Sonic hedgehog (SHH) signaling plays an important role during normal mammary gland development and it has been recently demonstrated that this signaling pathway is activated in breast carcinoma and that it regulates the behavior of breast cancer stem cells. The SHH pathway therefore constitutes a therapeutic target for the development of new breast cancer therapeutics.

The SHH gene belongs to a human gene family with three genes that encode secreted glycoproteins implicated in multiple developmental processes, including the regulation of cell identity, proliferation and survival (Ingham & McMahon (2001) *Genes Dev.* 15:3059-3087). SHH is the most widely expressed of the family and the one that has been implicated in human cancer. SHH signals are conveyed intracellularly by the membrane proteins PATCHED (PTCH1) and SMOOTHENED (SMOH). In the absence of SHH, PTCH11 inhibits SMOH, thereby inhibiting the downstream transduction cascade. On binding of SHH to PTCH1, inhibition is released, SMOH signals, and a macromolecular complex that is associated with the cytoskeleton is activated. The reception of the SHH signal in the responding cell results in the activation of target genes through the transcription factors of the GLI family. Three GLI genes have been identified that code for proteins with partially divergent functions (Ruiz i Altaba, et al. (2003) *Curr. Opin. Genet. Dev.* 13:513-521). In general, GLI1 acts primarily as an activator, GLI2 as both an activator and repressor, and GLI3 mostly as a repressor (Ruiz i Altaba, et al. (2003) supra; Jacob & Briscoe (2003) *EMBO Rep.* 4:761-765). However, these functions are context-dependent (Bai, et al. (2004) *Dev. Cell.* 6:103-115; Karlstrom, et al. (2003) *Development* 130:1549-1564; Persson, et al. (2002) *Genes Dev.* 16:2865-2878; Ruiz i Altaba (1998) *Development* 125:2203-2212). SHH-GLI pathway signaling has been shown to be blocked by interaction of a plant-derived alkaloid known as cylopamine with SMOH (Chen, et al. (2002) *Genes Dev.* 16:2743-2748).

The first link of SHH to cancer was the identification of mutations in the PTCH1 gene in patients with Gorlin's or Basal Cell Nevus Syndrome (Hahn, et al. (1996) *Cell* 85:841-851; Johnson, et al. (1996) *Science* 272:1668-1671). These patients develop a variety of tumors at higher frequency and with an earlier onset that normal, including basal cell carcinoma (BCC) of the skin and medulloblastoma of the cerebellum. It has also been shown that SHH signaling is active in the majority of sporadic BCCs (Dahmane, et al. (1997) *Nature* 389:876-881) and in brain tumors, including medulloblastomas and gliomas (Dahmane, et al. (2001) *Development* 128:5201-5212; Berman, et al. (2002) *Science* 297:1559-1561; Clement, et al. (2007) *Curr. Biol.* 17:165-172). The SHH signaling pathway has also been linked to prostate cancer (Karhadkar, et al. (2004) *Nature* 431:707-712; Sanchez, et al. (2004) *Proc. Natl. Acad. Sci. USA* 101:12561-12566; Sheng, et al. (2004) *Mol. Cancer.* 3:29), small cell lung cancer (Watkins, et al. (2003) *Nature* 422:313-317), lung adenocarcinoma (Yuan, et al. (2007) *Oncogene* 26:1046-1055), melanoma (Stecca, et al. (2007) *Proc. Natl. Acad. Sci. USA* 104:5895-5900), and pancreatic cancer (Berman, et al. (2003) *Nature* 425:846-851). Importantly, treatment of cancer cells derived form these various types of cancer with cyclopamine in vitro or in vivo induces a decrease in proliferation, an increase of apoptosis, or a decrease of metastasis. The effects of cyclopamine are specific as they are rescued by expression of GLI1, which acts downstream of SMOH in the signaling pathway; further, the effects of cyclopamine are mimicked by inhibition of SMOH by RNA interference (Clement, et al. (2007) *Curr. Biol.* 17:165-172; Stecca, et al. (2007) *Proc. Natl. Acad. Sci. USA* 104:5895-5900).

Studies have also linked the SHH signaling pathway with mammary gland function and breast cell proliferation. Studies in transgenic mice, specifically Gli2$^{+/-}$ and Ptc1$^{+/-}$, have demonstrated a role for SHH signaling in mammary gland development (Lewis, et al. (2001) *Dev. Biol.* 238:133-144; Lewis, et al. (1999) *Development* 126:5181-5193), although the precise role of the SHH signaling pathway in this process remains to be elucidated. Moreover, constitutive activation of the SHH pathway in transgenic mice through the expression of activated SMOH in the mammary epithelium results in increased proliferation of progenitors cells and leads to ductal dysplasia (Moraes, et al. (2007) *Development* 134:1231-1242). In humans, mammary stem cells have active SHH signaling and treatment of mammosphere cultures, generated from mammary stem cells, with recombinant SHH induces an increase in the number of sphere-initiating cells and mammosphere size (Liu, et al. (2006) *Cancer Res.* 66:6063-6071). Addition of cyclopamine to mammospheres has the inverse effects (Liu, et al. (2006) supra). Malignant mammospheres obtained from human breast cancer samples respond in a similar manner to modulation of SHH signaling (Liu, et al. (2006) supra). Thus, as in the case of gliomas (Clement, et al. (2007) *Curr. Opin. Biol.* 17:165-172), stem cells in breast cancers appear to require an active SHH pathway for continued proliferation and survival.

There is a need for new therapeutics for treatment of cancer, including breast cancer, and the SHH pathway is an attractive target. Although cyclopamine has been shown to be effective on treatment of cancer using a variety of mouse models and human cells are also sensitive, cyclopamine is difficult to synthesize and its purification from corn lillies (*Veratrum californicum.*) is expensive. A number of derivatives have been produced, some slightly more active such as KAAD-cyclopamine (Sicklick, et al. (2006) *Carcinogenesis* 27(4):748-57). Other derivatives of cyclopamine are disclosed, e.g., in U.S. Pat. No. 6,432,970; 6,291,516; 6,552,016; 6,686,388; and 7,230,004 as well as U.S. Patent Application Nos. 2006/0074030, 2004/0060568, 2004/0110663, 2004/0127474, and 2006/0020020; Chen et al. (2002. *Proc. Natl. Acad. Sci. USA* 99:14071-14076); and Frank-Kamenetsky, et al. (2002) *J. Biol.* 1:10).

However, there remains a need for new derivatives of cyclopamine that are easier to produce and have greater activity against cancer.

SUMMARY OF THE INVENTION

The present invention is a steroid-derived cyclopamine analog that inhibits sonic hedgehog signaling. In particular embodiments, the steroid contains a C-17 spiro ring and is derived from an estrane (e.g., estradiol, estriol, or estrone), androstane (e.g., testosterone, dihydrotestosterone, or androsterone), pregnane, or cholestane. In specific embodiments, the analog has a structure as set forth in Table 1. In other embodiments, the steroid-derived cyclopamine analog is in admixture with a pharmaceutically acceptable carrier.

The present invention also provides a method for inhibiting sonic hedgehog signaling in a cell by contacting the cell with a steroid-derived cyclopamine analog of the present invention.

A method for preventing or treating cancer is also embraced by the present invention. This method involves administering to a subject in need of treatment an effective amount of a composition containing a steroid-derived cyclopamine analog of the invention thereby preventing or treating the subject's cancer. In particular embodiments, the cancer is breast cancer, prostate cancer, small cell lung cancer, lung adenocarcinoma, melanoma, pancreatic cancer, basal cell carcinoma, medulloblastoma, or meningioma, wherein metastatic cancer are also included.

The present invention further features a method for synthesizing a steroid-derived cyclopamine analog of the invention. Said method involves (a) contacting a steroid with a conjugate base, and (b) subjecting the product of (a) to Buchwald-Hartwig cyclization thereby synthesizing a steroid-derived cyclopamine analog.

DETAILED DESCRIPTION OF THE INVENTION

Figure 1A:
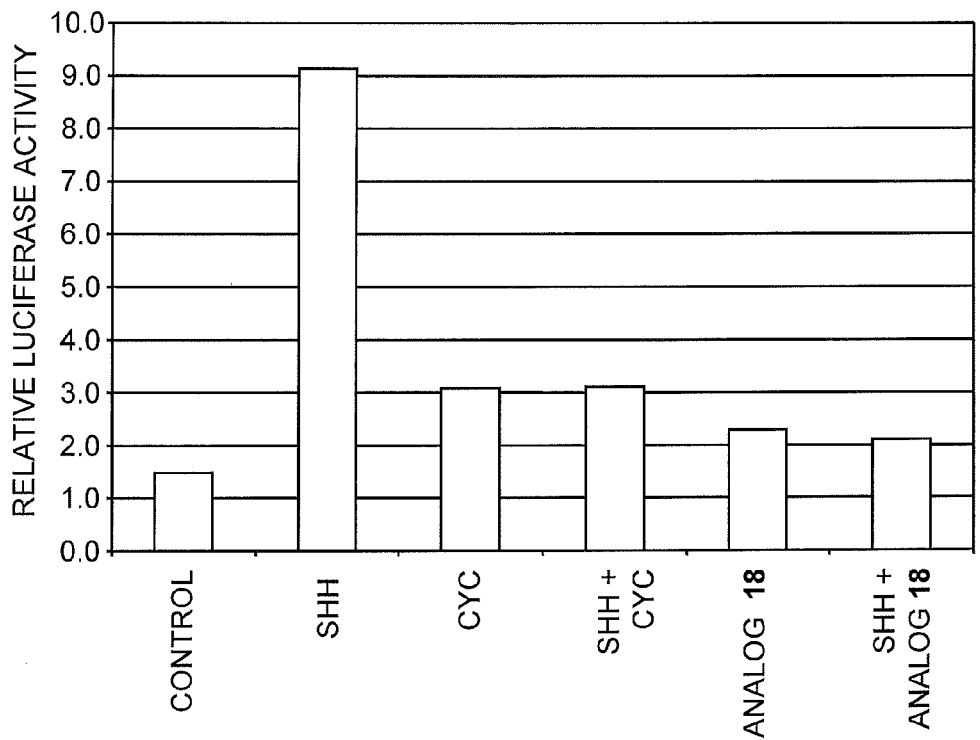
FIG. 1 shows the inhibition of SHH-induced activation of GLI-dependant firefly luciferase by cyclopamine (CYC) and steroid-derived cyclopamine analog 18 at 10 (FIG. 1A), 5 (FIG. 1B), and 2.5 µM (FIG. 1C) as compared to control.

A series of novel steroid-derived cyclopamine analogs have now been synthesized, which block the SHH signaling pathway. These analogs find application in inhibiting SHH signaling in a cell and as therapeutics for the prevention and treatment of cancer, including breast cancer. In the context of the present invention, a "steroid-derived cyclopamine analog" is a compound that has been synthesized through a steroid modification pathway (i.e., using a steroid as a reactant) and is structurally similar to cyclopamine. In particular embodiments, a cyclopamine analog of the invention contains a C-17 spiro ring, which effectively orients the E/F heterobicyclic moiety relative to the A-ring oxygenation in the conformation that is required for the inhibition of Hedgehog signaling. In this regard, the steroid-derived cyclopamine analog also shares one or more biological activities of cyclopamine. Such biological activities include protein binding specificity, inhibition of SHH signaling, or decreasing SHH-mediated cell proliferation and survival.

Several different approaches were considered for the synthesis of cyclopamine as well as cyclopamine analogs. The first approach involved epoxide opening. Cyclopamine 1 (Scheme 1) is a complex structure composed of six rings and ten stereogenic centers. As outlined below, it was contemplated that the most efficient route would be a convergent one, involving the connection of the two fragments 7 and 8. In the synthetic direction, Stille coupling of vinyl iodide 7 and 8 would give 6 (De Souza, (2006) Curr. Organ. Synth. 3:313-326). Sharpless directed epoxidation of 6 would give 5 (Sharpless & Verhoeven (1979) Aldrichim. Acta 12:63-74). Selective PMB removal (CAN) in the presence of the silyl ethers (R'=TBDMS) or carbonate protecting groups for the C-5/C-6 diol would lead to the formation of 4 on epoxide opening. Directed Crabtree-Stork hydrogenation of 4 would then give the C-20α methylated product 3 (Crabtree & Davis (1986) J. Organ. Chem. 51:2655-2661; Stork & Kahne (1983) J. Am. Chem. Soc. 105:1072-1073). Corey-Winter olefination of 3 (Corey & Winter (1963) J. Am. Chem. Soc. 85:2677-2678) would then give 2, which on deketalization and selective reduction would afford 1.

SCHEME 1

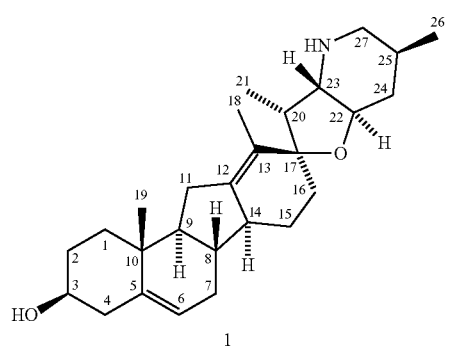

1

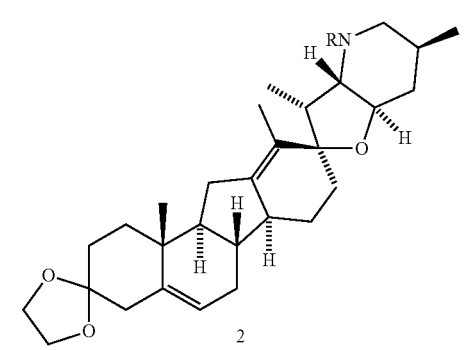

2

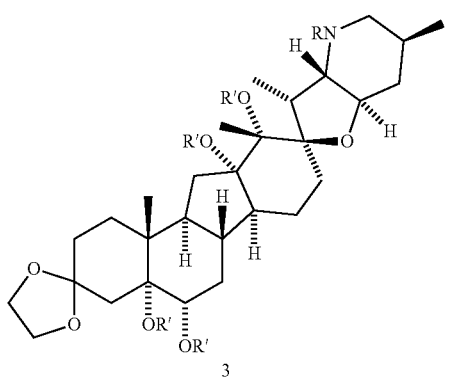

3

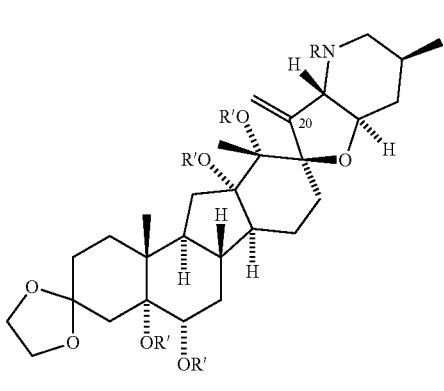

4

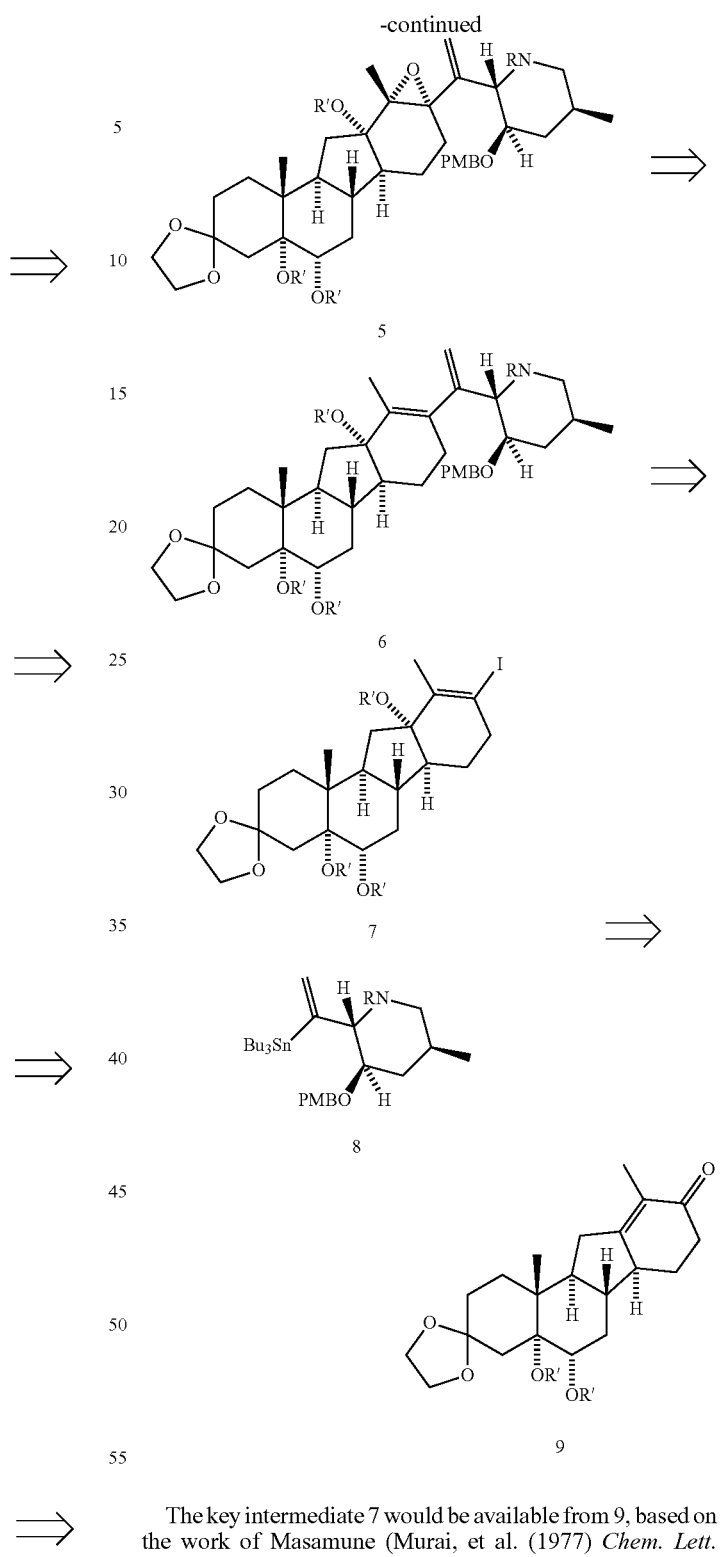

The key intermediate 7 would be available from 9, based on the work of Masamune (Murai, et al. (1977) *Chem. Lett.* 235-236). Annulation of the C and D rings of cyclopamine onto a bicyclic core has been previously described by Brown (Brown & Lebreton (1986) *Tetrahed. Lett.* 27:2595-2598). The same protocol would be applied to the synthesis of 9, using the optically active form of the Wieland-Mischer ketone as the starting material (Heathcock, et al. (1982) *J. Am. Chem. Soc.* 104:1907-1917). The preparation of 8 is based on the synthesis of trans-pipecolic acid reported by Casiraghi (Battistini, et al. (1997) *Tetrahed. Assym.* 8:2975-2987). The innovations afforded by the realization of this construction include the first chemically synthesized cyclopamine and, more significant, the possibility of structural modification of both 7 and 8 to generate cyclopamine analogs for further structure activity relationship analysis.

An alternative approach to the synthesis of cyclopamine, referred to as the olefin metathesis route, is outlined in Scheme 2. Intramolecular olefin metathesis reaction of 11 would give 10 under the Grubbs conditions. The metathesis substrate 11 should be available from methylenation of 12, the product of reductive alkylation of with 14. The synthesis of 14 would be performed via manipulation of a suitably-substituted furan-Diels-Alder adduct (Ishibashi, et al. (1991) *Chem. Pharmaceut. Bull.* 39:2878-2882; Stajer, et al. (2004) *J. Org. Chem.* 3701-3706).

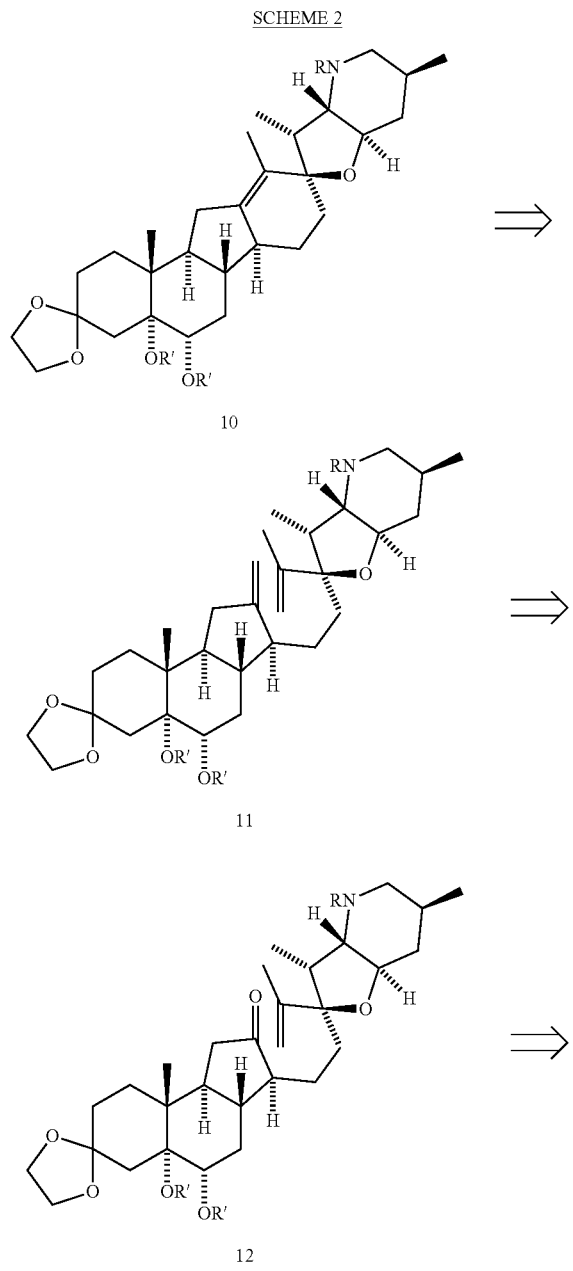

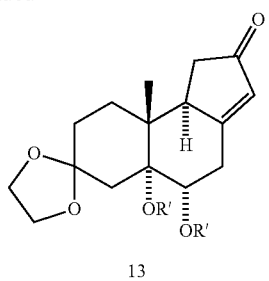

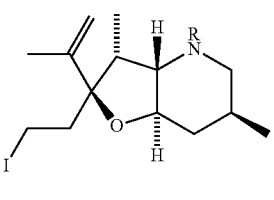

While the above methods would yield cyclopamine, a steroid-derived synthesis approach (Scheme 3) was employed for generating the cyclopamine analogs disclosed herein. In accordance with this method, a novel steroid-based analog, 18, was prepared. Addition of the conjugate base of bromopyridine 16 to the silyl ether of 15 gave 17, in which the anion added to the sterically less hindered a-face of the C-17 carbonyl of 15. Buchwald-Hartwig cyclization of 17 afforded, after disilylation, the desired product 18 in four steps from commercially available estrone 15.

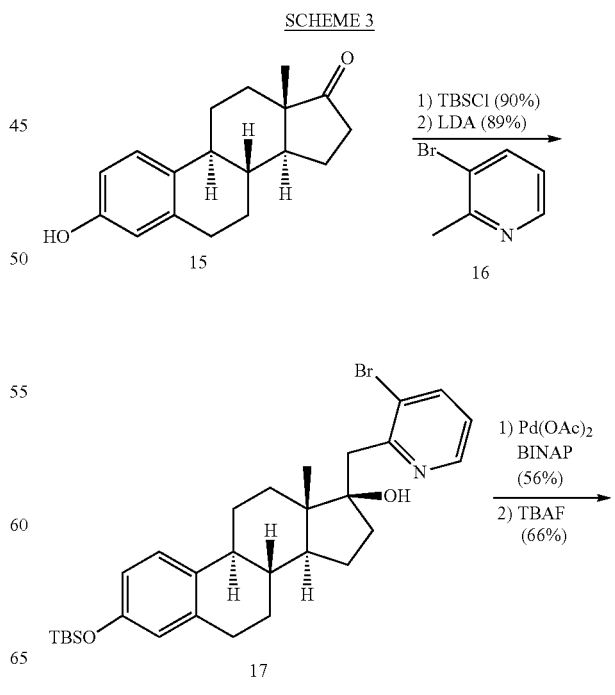

-continued

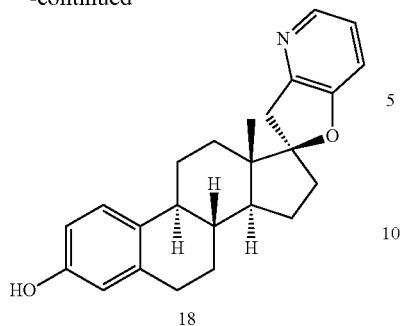

18

Cylopamine analogs have been shown to have different biological effects, as would be expected based on the basic principles of structure-activity relationship (SAR) that can be used to predict the biological reactivity, including toxicity, of chemicals with similar structures. For example, the difference in teratogenic potential between cyclopamine (active) 1 and the close structural analog tomatidine 15 (inactive) has been attributed to the difference in the orientation of the nitrogen atom relative to the steroid plane in 1 and 15.

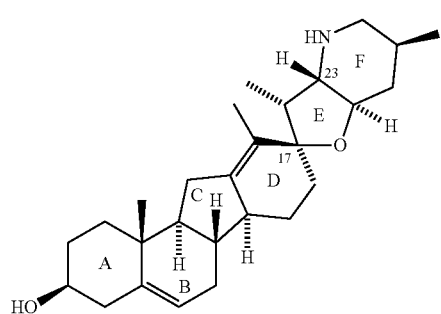

-continued

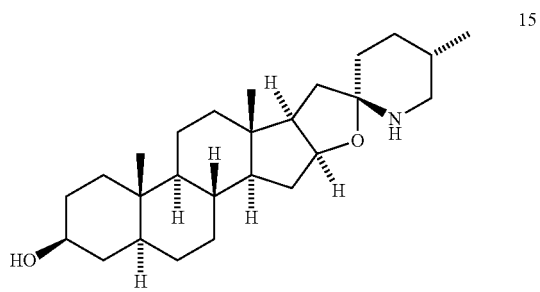

As a result, the C-nor-D-homo framework of 1 can be viewed as a scaffold that orients the E/F heterobicyclic moiety relative to the A-ring oxygenation in the conformation that is required for the inhibition of Hedgehog signaling. Accordingly, as shown in Table 1, alternate scaffolds were employed for the C-nor-D-homo steroidal framework of 1. Specifically, analogs 16 and 17 were designed based on the A-ring saturated and A-ring aromatic (i.e., estrone) "classical" 6/6/6/5 steroid frameworks. As illustrated in the energy minimized (Macromodel) structures below, the C-17 (spirocyclic) stereochemistry of 16 is critical to the congruence with cyclopamine 1, as 38, the C-17 epimer of 16, does not overlap with 1.

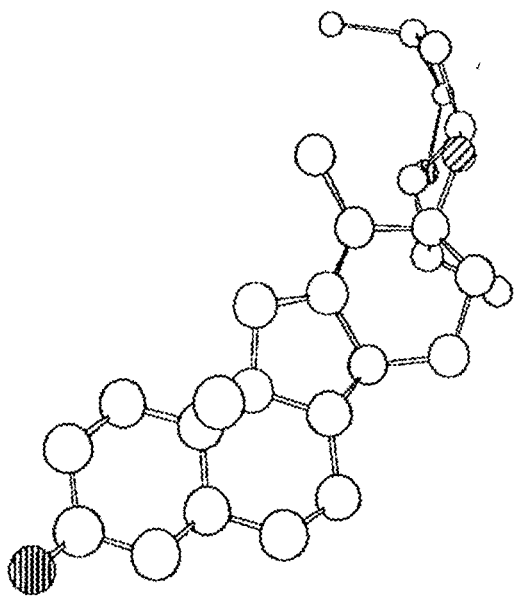

-continued

16

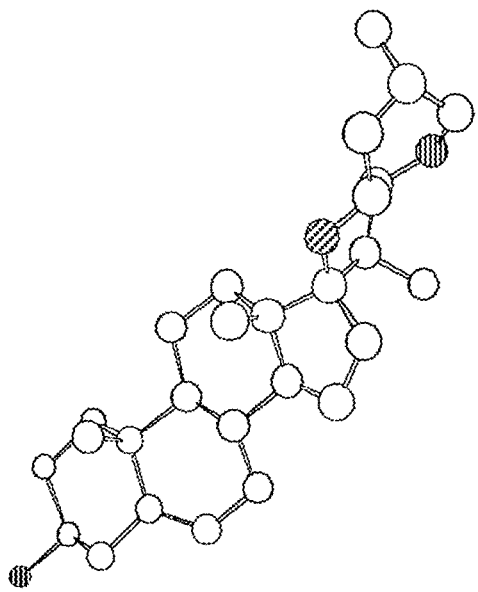

38

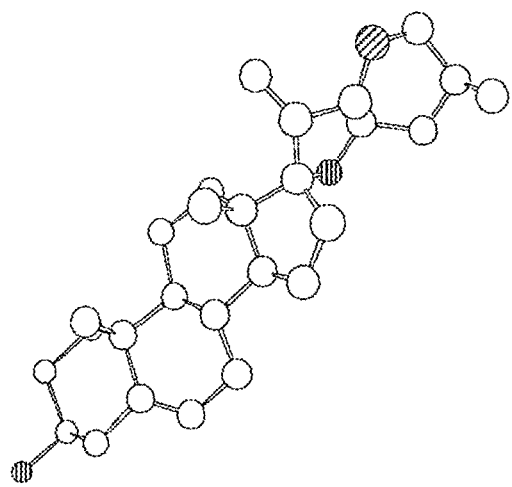

Two complementary approaches for the elaboration of the commercially available steroid adrenosterone were also examined. Amination of the known steroidal lactone (Wuts & Ritter (1989) *J. Org. Chem.* 54:5180-5182) (in which the ketone is protected as the corresponding ketal) would give 19 and its C-23 epimer, so that the effect of the nitrogen stereochemistry (and substituents R and R') on the biological activity of 19 could be examined. It should be noted that KAAD-cyclopamine, the product of attachment of a long alkyl chain onto the nitrogen atom of cyclopamine, is the most potent Hedgehog inhibitor discovered to date (Taipale, et al. (2000) *Nature* 406:1005-1009). The analogous substitutions would be effected with both 19 and its C-23 epimer. The activity of 20 and 21, both of which lack the C-20 and C-25 methyl groups of both cyclopamine 1 and steroidal analogs 16 and 17 were examined in an effort to establish the minimal structural and stereochemical complexity that is required to effectively block Hedgehog signaling.

The preparation of F-ring aromatic (pyridyl) analogs of cyclopamine based on the natural steroid framework represented another important simplification of the structure of 1. The synthesis of 22 and 23, in which the A ring can be either aromatic (estrone precursor) or non-aromatic (adrenosterone precursor) was examined. The preparation of these analogs was based on the methodology developed by Buchwald (Anderson, et al. (2006) *J. Am. Chem. Soc.* 128:10694-10695) and Hartwig (Hartwig (2006) *Synlett* 1283-1294). Addition of the conjugate base of commercially available 3-chloro-2-methylpyridine (3-chloro-2-picoline; Houminer & Williams (1983) *J. Org. Chem.* 48:2622-2625) to the D-ring carbonyl group of either estrone or adrenosterone, respectively, led to the formation of the requisite C-17 stereochemistry, as predicted based on extensive precedent in the steroid literature (VanRheenen & Shepard (1979) *J. Org. Chem.* 44:1582-1585). Intramolecular Buchwald-Hartwig reaction afforded 22 and 23, respectively. The preparation of cyclopamine analogs in just two chemical steps from commercially available starting materials, as described herein, represented an important innovation. Moreover, when compared to cyclopamine, the instant analogs do not contain the allylic ether present in cyclopamine that confers metabolic, i.e., acid, instability.

Accordingly, the present invention provides novel cyclopamine analogs and a method for producing the same. The cyclopamine analogs disclosed herein can be produced from any suitable steroid. For the purposes of the present invention, a steroid is a terpenoid lipid characterized by a carbon skeleton with four fused rings, generally arranged in a 6/6/6/5 fashion. Steroids can be classified based on taxonomic or functional characteristics or their chemical composition. In this regard, steroids composed of 18 carbon atoms are classified as estranes, steroids composed of 19 carbon atoms are classified as androstanes, 22 carbon atoms as pregnanes or cholanes, and 27 carbon atoms as cholestanes. In particular embodiments of the present invention, the steroid-derived cyclopamine analogs are synthesized from an estrane or androstane steroid. In this regard, an "estrane or androstane steroid-derived cyclopamine analog" has a 6/6/6/5 framework structure of an estrane or androstane steroid. Exemplary estranes include, but are not limited to estradiol, estriol, and estrone. Exemplary androstanes include, but are not limited to, testosterone, dihydrotestosterone, androsterone. In particular embodiments, the instant cyclopamine analogs are derived from estrone or androsterone. Steroids of use in the present invention can be obtained from a commercial source or synthesized using conventional methods. Moreover, conventional methods can be employed to generate the C17 ketone for steroids lacking the same.

In accordance with the synthesis method of the present invention, a steroid-derived cyclopamine analog is produced by contacting an estrane or androstane steroid with a conjugate base. For the purposes of the present invention, a conjugate base is preferably a pyridine derivative. In particular embodiments the pyridine derivative is a halopyridine of Formula I:

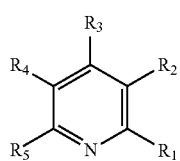

Formula I wherein at least one of $R_2$ or $R_4$ is a halo group including, bromo, chloro, iodo, or fluoro; and at least one of $R_5$ or $R_1$ is methyl. Wherein one of $R_2$ or $R_4$ is a halo group, the other of $R_2$ or $R_4$ can be a hydrogen, halogen, alkyl, alkenyl, alkynyl, aryl, hydroxyl, =O, =S, alkoxyl, silyloxy, amino, nitro, thiol, amine, imine, amide, phosphoryl, phosphonate, phosphine, carbonyl, carboxyl, carboxamide, anhydride, silyl, ether, thioether, alkylsulfonyl, arylsulfonyl, selenoether, ketone, aldehyde, or ester. Similarly, wherein one of $R_5$ or $R_1$ is methyl, the other of $R_5$ or $R_1$ can be a hydrogen, halogen, alkyl, alkenyl, alkynyl, aryl, hydroxyl, =O, =S, alkoxyl, silyloxy, amino, nitro, thiol, amine, imine, amide, phosphoryl, phosphonate, phosphine, carbonyl, carboxyl, carboxamide, anhydride, silyl, ether, thioether, alkylsulfonyl, arylsulfonyl, selenoether, ketone, aldehyde, or ester. Moreover, $R_3$ can be a hydrogen, halogen, alkyl, alkenyl, alkynyl, aryl, hydroxyl, =O, =S, alkoxyl, silyloxy, amino, nitro, thiol, amine, imine, amide, phosphoryl, phosphonate, phosphine, carbonyl, carboxyl, carboxamide, anhydride, silyl, ether, thioether, alkylsulfonyl, arylsulfonyl, selenoether, ketone, aldehyde, or ester.

Exemplary conjugate bases of use in accordance with the synthesis method disclosed herein include, but are not limited to, 5-bromo-6-methylpyridine, 3-chloro-2-methylpyridine, 5-chloro-6-methylpyridine, and 3-fluoro-2-methylpyridine.

As will be appreciated by the skilled artisan, free reactive groups (e.g., OH), which are not to be reacted with the conjugate base, can be protected by conventional methods, e.g., as illustrated herein.

Upon addition of the conjugate base to the steroid framework, conventional intramolecular Buchwald-Hartwig cyclization is employed to produce the E/F heterobicyclic moiety. Such intramolecular reactions can be performed according to the reaction conditions shown in Scheme 3. Advantageously, the resulting cyclopamine analogs of the present invention maintain the C-17 (spirocyclic) stereochemistry of cyclopamine.

Using the synthesis method disclosed herein, a series of novel, highly functionalized analogs of cyclopamine were prepared from commercially available steroidal precursors in a simplified procedure. These exemplary analogs are set forth herein in Table 1.

TABLE 1

Analog

TABLE 1-continued
Analog
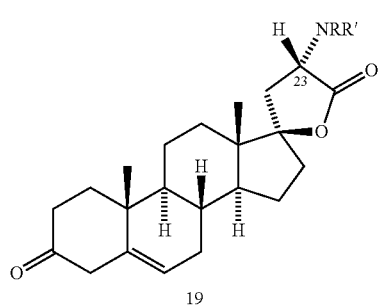
19
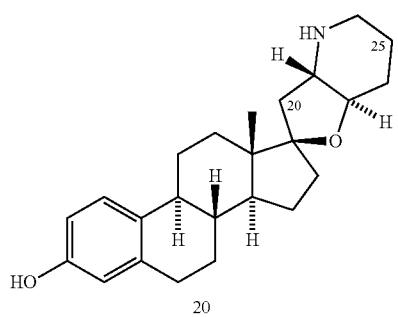
20
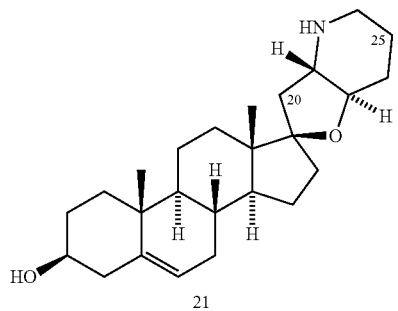
21
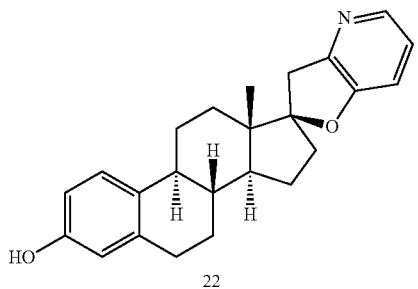
22
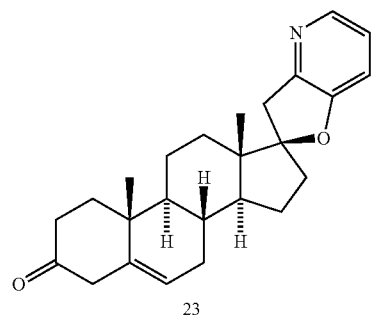
23
TABLE 1-continued
Analog
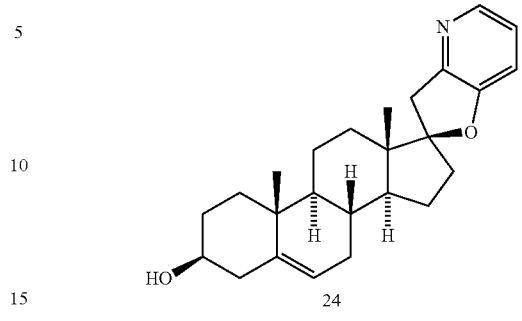
24
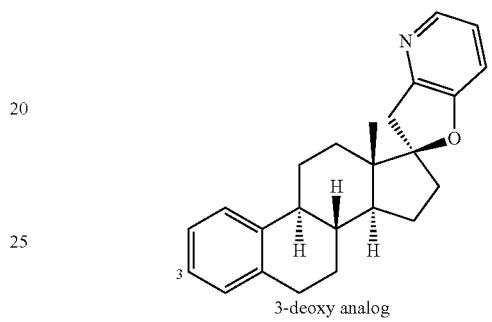
3-deoxy analog
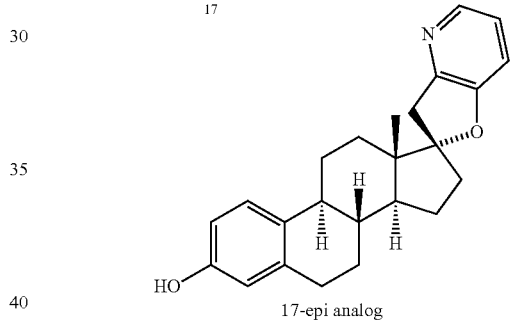
17-epi analog
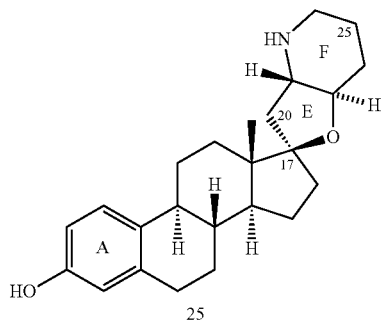
25
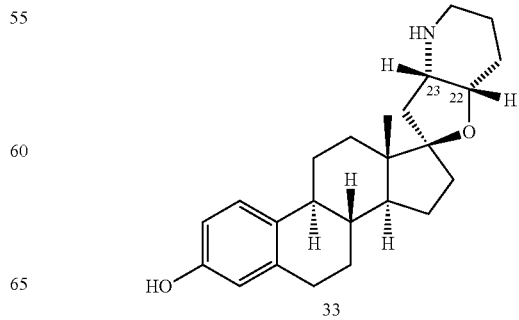
33

TABLE 1-continued

Analog

[Structure of analog 37: steroid structure with HO- on A ring, and HN-containing pyrrolidine-like substituent with numbered positions 22, 23, and O]

37

The use of commercially available precursors in the synthesis method disclosed herein provides an advantage of ease of synthesis and control over purity as compared to isolation and purification of cyclopamine from natural sources. The cyclopamine analogs of the present invention find application in inhibiting sonic hedgehog signaling and in the prevention and treatment of various cancers, including breast cancer, or for use in prevention and treatment of any disease shown to be linked to SHH signaling pathways.

To demonstrate the biological activity and efficacy of the steroid-derived cyclopamine analogs of the present invention, the analogs shown in Table 1 were subjected to a battery of tests that are commonly used to assess effects on SHH activity and to determine specificity.

Figure 1B:
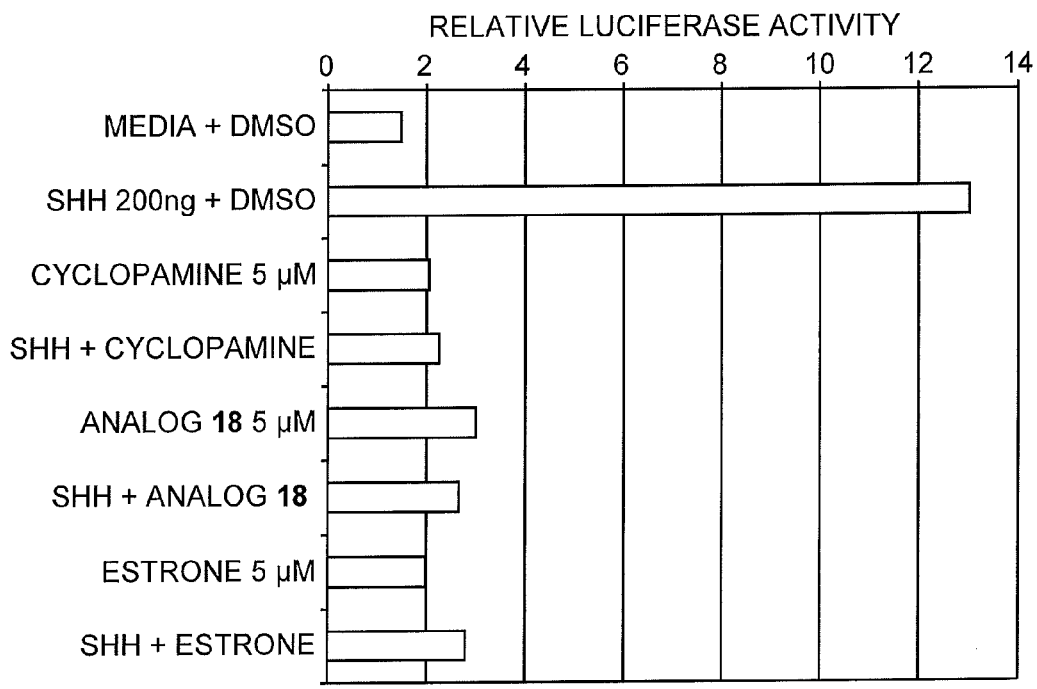
Figure 1C:
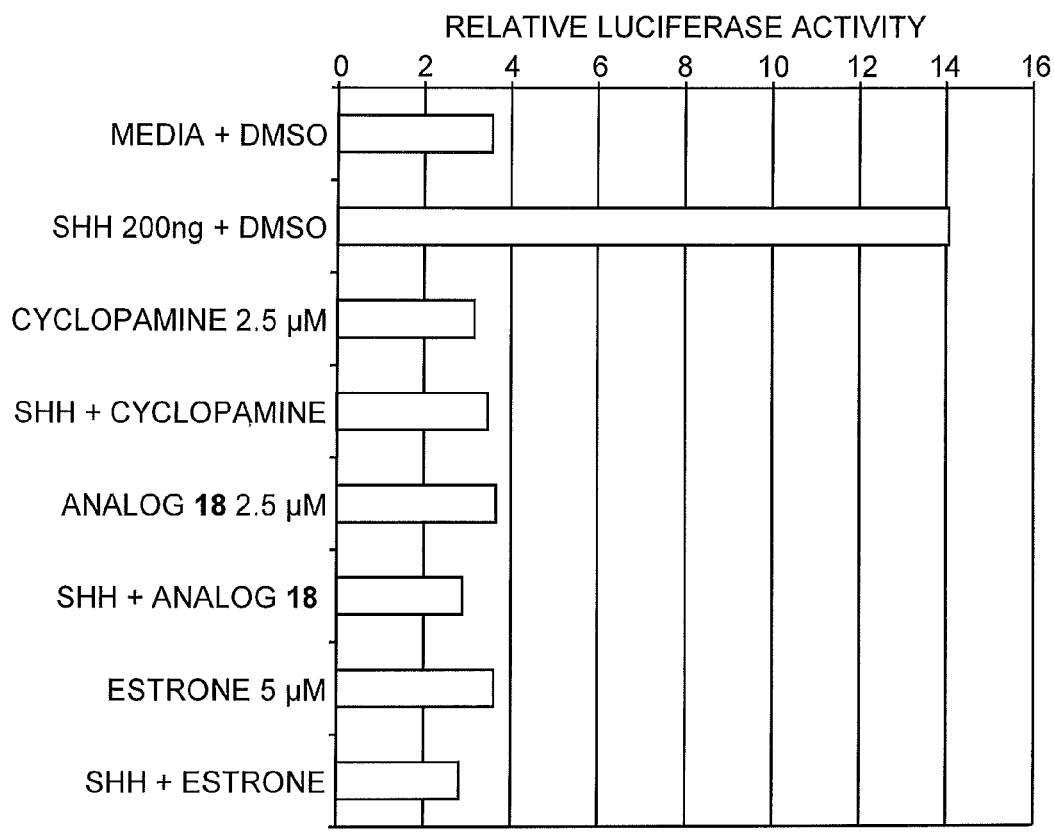

One screen involved examining the activation of the SHH pathway using the well-established cell line, SHH-Light2 cells. This cell line is a 3T3 clone that stably expresses a GLI-dependant firefly luciferase (Taipale, et al. (2000) *Nature* 406:1005-1009). Treatment of these cells with recombinant SHH activates GLI-dependant firefly luciferase and this SHH-induced activation has been shown to be inhibited when cells are also treated with cyclopamine (Taipale, et al. (2000) supra). Concentrations of each analog, ranging from 20 μM to 2.5 μM, were tested. SHH-Light2 cells were seeded 24 hours prior to treatment. They were then cultured for an additional 48 hours in standard serum-containing media prior to analysis. GLI-binding site luciferase activities were measured using a commercially available luciferase reporter assay system. Treatment of SHH-Light2 cells with recombinant SHH (200 ng) resulted in strong induction of reporter activity. $IC_{50}$ values were determined and were compared to that of cyclopamine in the same assay in order to determine which of the new cylcopamine analogs had the highest levels of SHH inhibitory activity. The results of this analysis for analog 18 indicated that this analog effectively inhibited SHH activity at 10 μM, which was comparable to cyclopamine (FIG. 1A). At lower concentrations of 5 μM and 2.5 μM, analog 18 inhibited SHH activity comparable to cyclopamine (FIGS. 1B and 1C, respectively).

Figure 2:
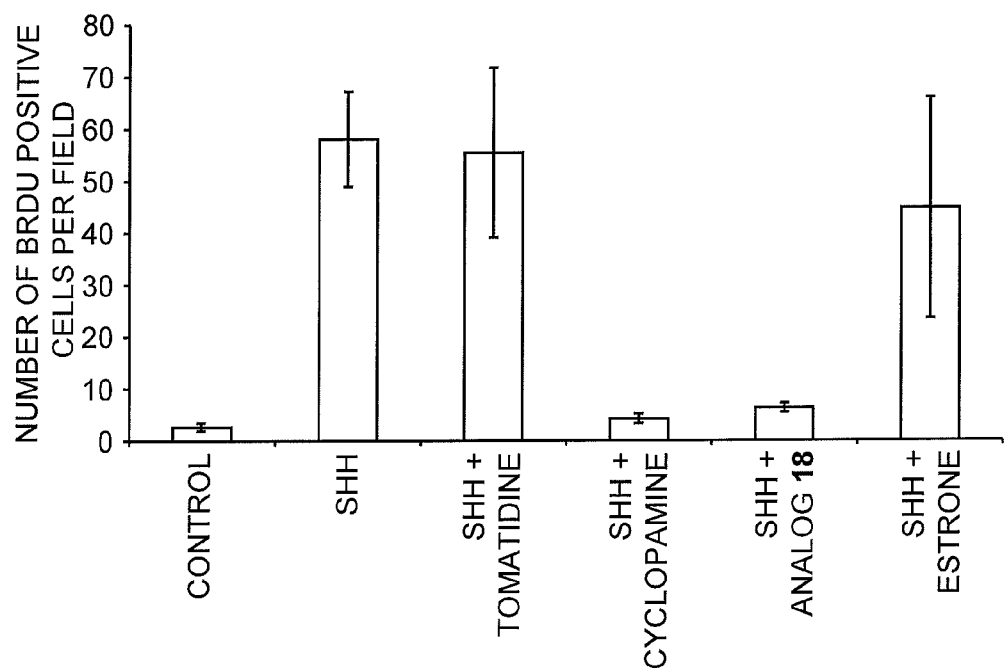
FIG. 2 shows the inhibition of SHH-induced granule neuron precursor (GNP) proliferation by cyclopamine and steroid-derived cyclopamine analogs. Purified GNPs were either not treated (CTR, n=4) or treated with SHH (600 ng/ml (n=4), alone or in combination with cyclopamine (10 µM, n=4), tomatidine (10 µM, n=4), analog 18 (10 µM, n=4) or estrone 15 (10 µM, n=2). BrdU-positive cells were counted with a fluorescent microscope using a 20× objective, wherein at least ten independent fields for each culture condition were counted per culture condition.
Figure 5:
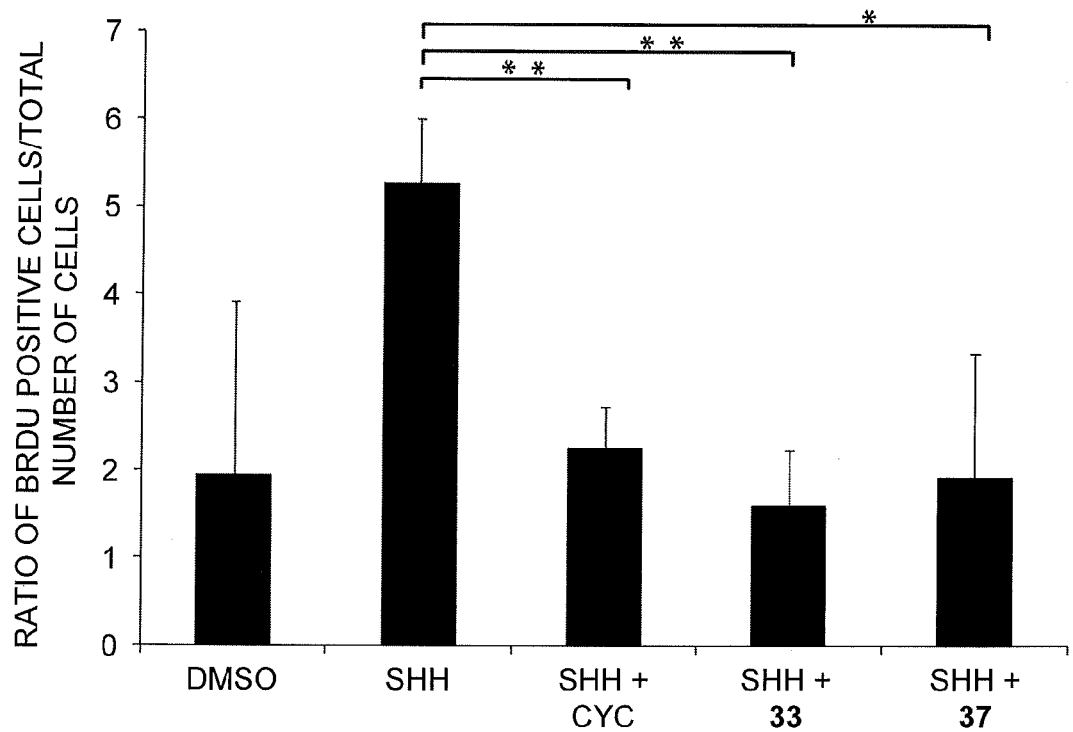
FIG. 5 shows that analogs 33 and 37 block SHH-induced GNP proliferation. Asterisk indicates the following p-value $*p<0.05$, $**p<0.01$.

It has previously been shown that SHH is a potent mitogen for granule neuron precursors (GNPs) purified from postnatal mouse cerebella (Dahmane & Ruiz I Altaba (1999) *Development* 126:3089-3200). This well-established system was used to test the instant steroid-derived cyclopamine analogs for their activity in inhibiting this proliferative response of GNPs to SHH. The activity of the cyclopamine analogs was compared with cyclopamine, which has been shown to block their proliferation. GNPs were purified from postnatal day 5 (P5) mouse cerebella, plated on poly-D-lysine in serum-free DMEM-F12 and treated with either SHH alone or SHH plus the analogs. Treatment with SHH and cyclopamine was used as a control for inhibition. The results of this analysis indicated that SHH alone enhanced cell proliferation while addition of cyclopamine significantly decreased cell proliferation for cells treated with SHH (FIG. 2). Tomatidine, an inactive cyclopamine analog, had no effect, whereas analogs 18, 33 and 37 were as potent as cyclopamine in inhibiting SHH-induced GNP proliferation (FIGS. 2 and 5). To rule out the possibility that the inhibition was an estrogenic effect, the activity of analog 18 was directly compared to that of estrone 15, and estrone did not produce the same effect.

Figure 3:
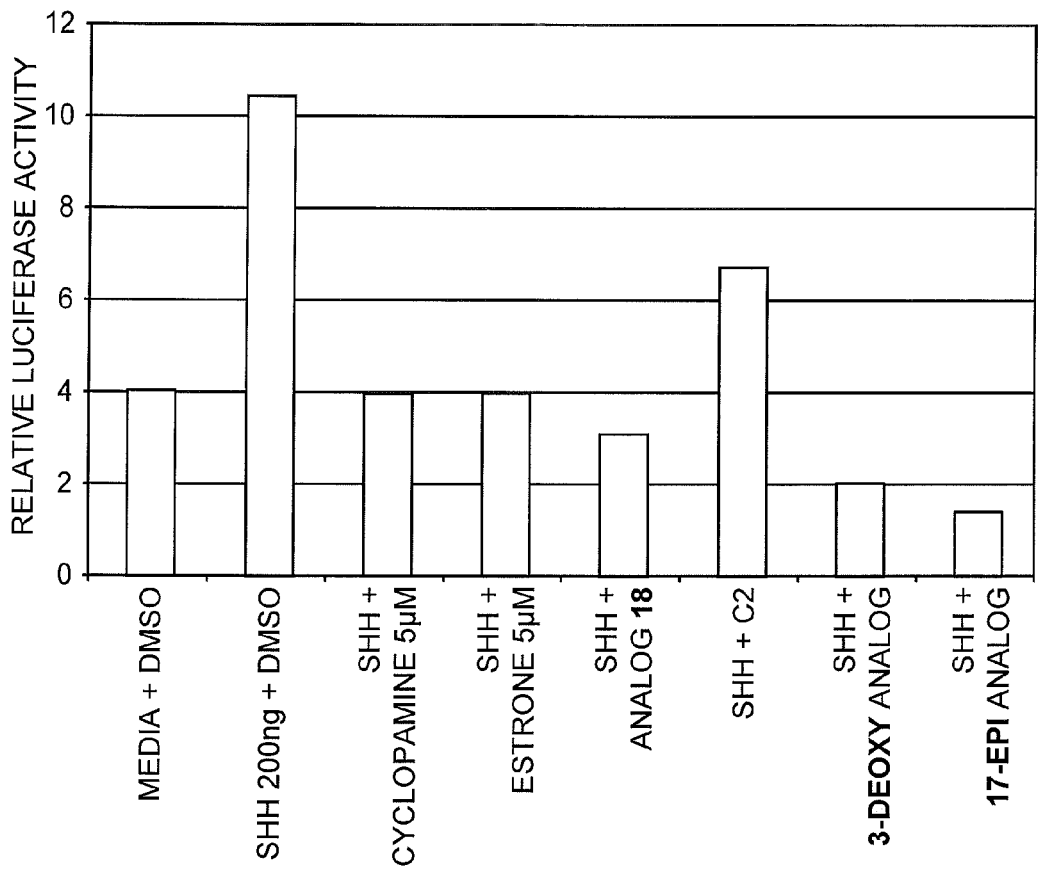
FIG. 3 shows the inhibition of SHH-induced activation of GLI-dependant firefly luciferase by cyclopamine and steroid-derived cyclopamine analogs. Shh-Light2 cells were seeded at 70% confluency in 24 wells, 24 hours prior to treatment. They were then cultured for an additional 48 hours in standard serum-containing media prior to analysis. GLI-binding site luciferase activities were measured using the luciferase reporter assay system with the luciferase kit (PROMEGA). Treatment of Shh-Light2 cells with recombinant SHH (200 ng) resulted in the strong induction of reporter activity, which was largely blocked by co-treatment with cyclopamine (5 µM). The same concentration of the selected analog 18, 3-deoxy analog, and 17-epi analog produced a similar or higher inhibition of SHH-induced activation.
Figure 4:
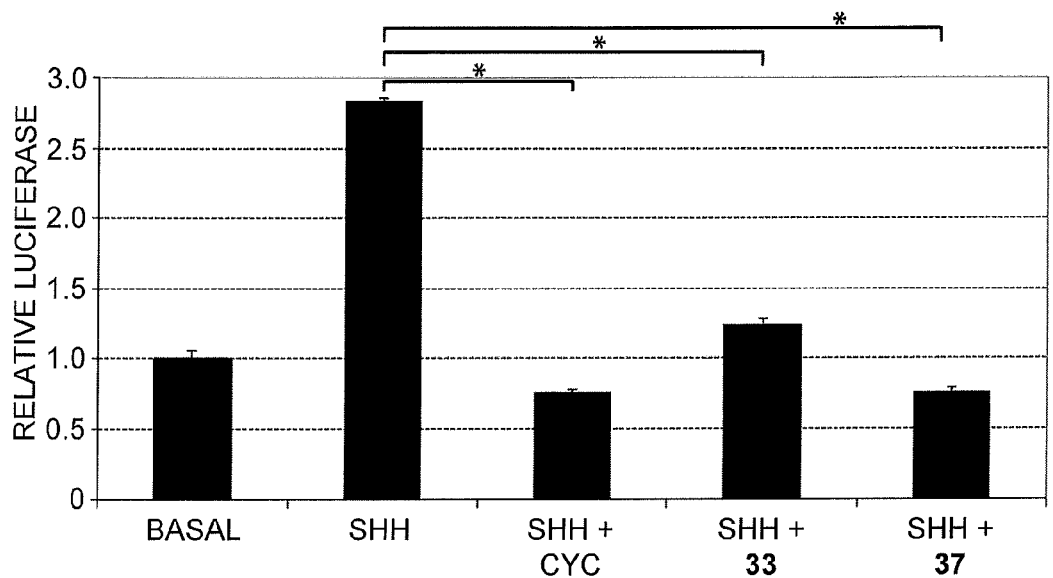
FIG. 4 shows that analogs 33 and 37 are potent inhibitors of the SHH-induced GLI-luciferase activity in SHH-Light2 cells. SHH-light2 cells were treated with SHH (600 ng/ml, R&D) alone or in combination with cyclopamine (CYC), analog 33 or analog 37. CYC, analog 33 and analog 37 were used at 5 mM. Asterisk indicates p-value $p<0.001$.

In similar analysis, treatment of Shh-Light2 cells with recombinant SHH (200 ng) resulted in the strong induction of reporter activity, which was largely blocked by co-treatment with cyclopamine (5 μM), wherein the same concentration of the selected analog 18, 3-deoxy analog, 17-epi analog, analog 33 and analog 37 produced a similar or higher inhibition of SHH-induced activation (FIGS. 3 and 4).

In addition to the screening assays described above, a series of additional tests can be used to further characterize the biological activity of the steroid-derived cyclopamine analogs of the present invention. For example, to examine the specificity of activity, rescue experiments are performed in cells expressing GLI1. Specificity is shown when effects are rescued by GLI1, whereas any non-specific effects are not reversed by GLI1.

Moreover, the blockade of SHH-induction of alkaline phosphatase activity in mouse cells can be determined. Treatment of mouse C3H10T½ cells with SHH (or transfection with GLI1 or GLI2, which can mediate SHH signals), leads to their osteogenic differentiation and the expression of alkaline phosphatase (Roessler, et al. (2003) *Proc. Natl. Acad. Sci. USA* 100:13424-13429; Ruiz I Altaba, (1999) *Development* 126:3205-3216). Therefore, it can be determined whether, like cyclopamine, SHH-mediated alkaline phosphatase expression can be blocked upon treatment with a cyclopamine analog disclosed herein.

Biological activity of the analogs of the invention can also be analyzed in breast cancer cells to demonstrate therapeutic efficacy. Previous studies have shown that breast cancer stem cells respond to cyclopamine. Therefore, cancer mammospheres, prepared form human breast cancer samples, are cultured (Liu, et al. (2006) *Cancer Res.* 66:6063-6071) and exposed to the steroid-derived cyclopamine analogs of the present invention. Medical history, cancer type, stage and other parameters of the breast cancer samples are then correlated with the inhibitory activity of the analogs.

Conventional cancer cell lines can also be employed to demonstrate the efficacy of an analog of the invention. For example, activity of SHH pathway can be assessed by monitoring the expression of GLI1 in the presence and absence of the analog. Cell lines of use in this analysis include the MCF7, DAOY and T47D cell lines.

In addition to growth in situ, metastasis is a major problem in breast cancer. It has been shown that systemic cyclopamine treatment in mice injected with metastatic melanoma cells blocks metastatic growth (Stecca, et al. (2007) *Proc. Natl. Acad. Sci. USA* 104:5895-5900). Therefore, the steroid-derived cyclopamine analogs of the present invention can be analyzed for anti-metastatic potency as well as anti-proliferative and pro-apoptotic activities. Accordingly, experiments are performed to test for cyclopamine analog-mediated inhibition of common breast cancer metastases (e.g., lung, liver, brain) after tail vein injection of metastatic breast cancer cells in mice. Breast cancer cell lines whose metastatic properties (4T1) have been characterized, and that stably express Luciferase are employed to visualize in vivo the metastatic cells. Metastases development is examined 1-2 weeks following injection by injecting D-luciferin to anesthesized mice and image analysis.

Another screening assay involves in vivo treatment of chick embryos. Treatment of developing chick embryos (HH stage 10) with cyclopamine has been shown to lead to a cyclopic phenotype typical of loss of SHH signalling (Cooper, et al. (1998) *Science* 280:1603-1607). This assay can also provide a measure of the potential toxicity of the analogs of the present invention.

Steroid-derived cyclopamine analogs of the invention can also be tested using a tumor mouse model that has been shown to react to either cyclopamine (Sanchez & Ruiz I Altaba (2005) *Mech. Dev.* 122:223-230) or a small drug targeting the SHH pathway (Romer, et al. (2004) *Cancer Cell* 6:229-240). $Ptc1^{+/-} p53^{-/-}$ mice develop medulloblastoma within a month after birth and die at 2 months on average. These mice represent an excellent model to test for effectiveness of the analogs of the present invention to treat tumors in vivo. Mice are administered the analogs orally in their diet or are injected intraperitoneally, and brain tumor development is assayed both with behavioural methods (circling, abnormal gait, etc) and by histological examination.

Furthermore, the analogs of the present invention can be tested in a nude mouse model with human breast cancer xenografts. Analogs are tested on orthotopical grafts of human breast cancer cell lines and primary tumors. These experiments involve grafting human tumor cells to the mouse breast fat pads using, e.g., the "humanized" mouse mammary fat pad protocol which reflects human breast cancer (Kuperwasser, et al. (2004) *Proc. Natl. Acad. Sci. USA* 101:4966-4971; Proia & Kuperwasser (2006) *Nat. Protocol* 206-214). After the tumor has developed and attained a reasonable size, analogs are injected intra- and peri-tumorally or intraperitoneally and tumor size is measured daily with a calliper.

Having demonstrated the instant cyclopamine analogs can inhibit sonic hedgehog signalling, the present invention features in vitro and in vivo methods for using said cyclopamine analogs to inhibit sonic hedgehog signalling. Thus, in accordance with one embodiment, a cell (e.g., a cancer cell) is contacted with a cyclopamine analog in vitro and sonic hedgehog signalling in the cell is inhibited. In accordance with another embodiment, an effective amount of one or more steroid-derived cyclopamine analogs of the present invention are used in the preparation of a medicament for the prevention or treatment of a disease or condition mediated by sonic hedgehog signaling. When such a medicament is administered to a subject in need of treatment, e.g., a subject having or at risk of having a disease or condition mediated by sonic hedgehog signaling, the sonic hedgehog signalling pathway is inhibited and the disease or condition is prevented or treated. Various diseases or conditions mediated by sonic hedgehog signaling cell are well-known to those skilled in the art. Such disease and conditions are generally characterized as proliferative disorders such as breast cancer, prostate cancer, small cell lung cancer, lung adenocarcinoma, melanoma, pancreatic cancer, basal cell carcinoma (BCC), medulloblastoma, and meningiomas. Moreover, inhibition of the sonic hedgehog signaling pathway, as described herein, may be useful in inhibiting cancer metastasis.

The instant analogs may be particular useful in the prevention or treatment of medullablastoma. Medulloblastoma is a malignancy of the cerebellum with the highest incidence of all pediatric brain tumors and existing therapies are not optimal. Medulloblastomas are thought to recapitulate developmental events but in a deregulated fashion. It has been shown that the Sonic hedgehog (SHH) signaling pathway is critical for the development of the cerebellum where its deregulation can lead to medulloblastoma. This pathway is transduced in cells responding to the secreted factor SHH by the activation of zinc finger transcription factors of the GLI family. A tight regulation of this signaling pathway is thus critical not only for normal brain development but also during adulthood for homeostasis and for the prevention of tumor formation. In the developing cerebellum, SHH regulates the proliferation of granule cell precursors (GCPs) which are thought to be the cells at the origin of medulloblastomas.

Most medulloblastomas are sporadic, but they also occur in familial syndromes. Mutations in PATCHED1 (PTCH1), a negative regulator of SHH signaling, are associated with Gorlin's syndrome and also occur in sporadic medulloblastoma. Mice heterozygous for mutations in Ptc1 also develop medulloblastomas showing a higher penetrance on a p53 background. Mutations activating the SHH pathway may be found in approximately 10-25% of all sporadic medulloblastomas. However, alterations in this pathway through epigenetic events may greatly elevate this number. One possibility is that most human sporadic medulloblastomas may require sustained SHH signaling. Pharmacological inhibition of the SHH pathway in $Ptch1^{+/-}; p53^{-/-}$ mice inhibits medulloblastoma growth, indicating the utility of the instant analogs in preventing or treating medullablastoma.

Cyclopamine analogs of the invention can be administered by any suitable means, including parenteral, subcutaneous, intrapulmonary, and intranasal administration. Parenteral infusions include intramuscular, intravenous, intraarterial, or intraperitoneal administration. Cyclopamine analogs can also be administered by inhalation. Cyclopamine analogs may also be administered transdermally in the form of a slow-release cutaneous or subcutaneous implant for example, or orally in the form of capsules, powders or granules. Cyclopamine analogs can also be applied locally directly on the epidermis (e.g., topically), in the form of a cream or ointment, for example, in the case of BCC.

Generally, when used in the prevention or treatment of a disease or condition, the cyclopamine analogs of the invention are in admixture with a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The invention provides any pharmaceutical preparations and compositions containing one or more cyclopamine analogs of the invention for use in the method of the invention. The form will vary depending upon the route of administration. For example, compositions for injection can be provided in the form of an ampule, each containing a unit dose amount, or in the form of a container containing multiple doses.

Cyclopamine analogs can be formulated into the pharmaceutical composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery of the instant analogs may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the compounds of the invention may be controlled by altering the concentration of the macromolecule.

Another method for controlling the duration of action includes incorporating the cyclopamine analogs into particles of a polymeric substance such as polyesters, polyamino acids, hydrogels, polylactide/glycolide copolymers, or ethylenevinylacetate copolymers. Alternatively, it is possible to entrap cyclopamine analogs in micro-capsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

Example 1

Synthesis of the 17-Epi Analog

Using the synthetic method disclosed herein, a 17-epi analog was produced as illustrated in Scheme 4.

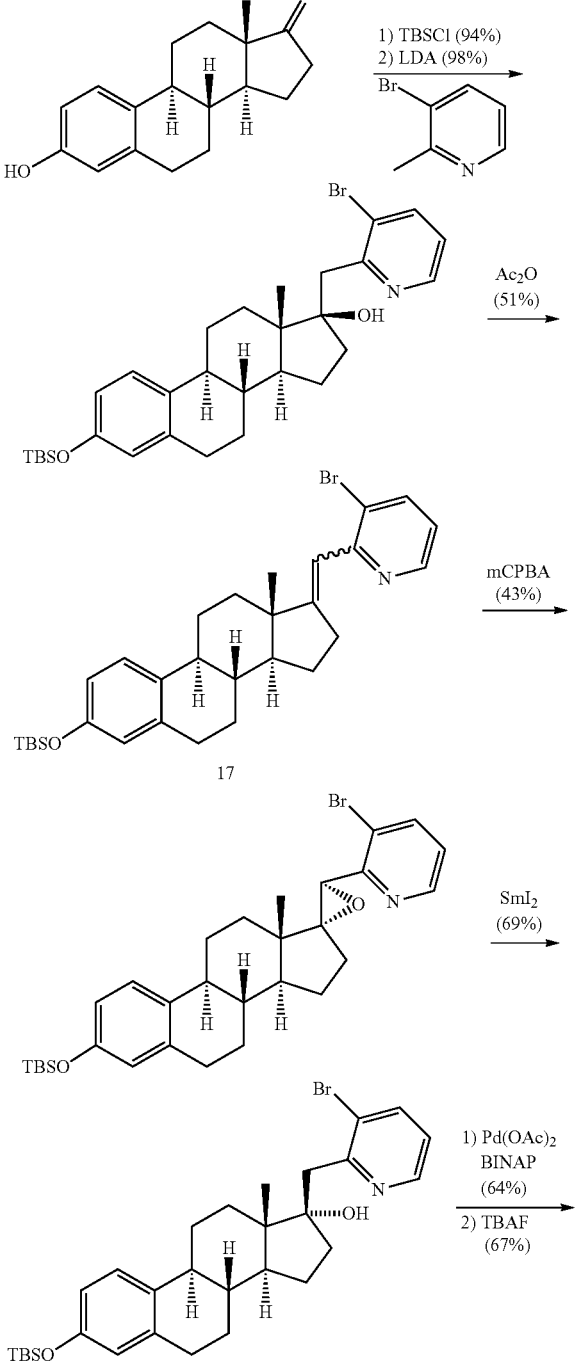

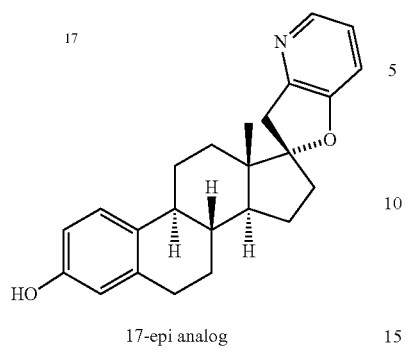

17-epi analog

Example 2

Synthesis of 3-Deoxy Analog

Using the synthetic method disclosed herein, a 3-deoxy analog was produced as illustrated in Scheme 5.

SCHEME 5

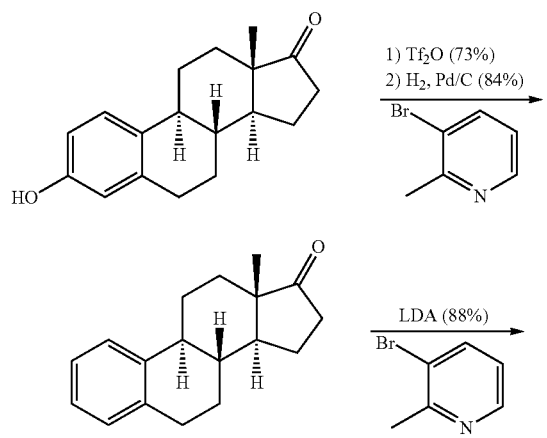

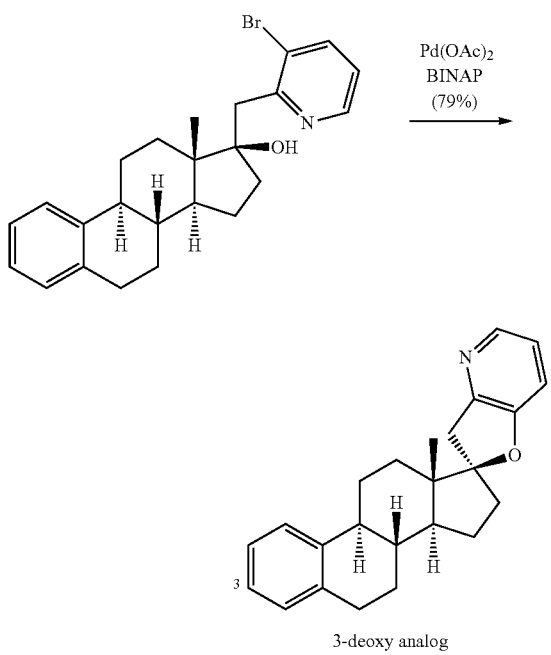

3-deoxy analog

Example 3

Synthesis of F-ring Saturated Analogs

While the direct reduction of the pyridine ring in 22 appeared to be the most direct approach to the synthesis of F-ring saturated analogs, i.e., 25, it was observed that the pyridine ring in 22 was resistant to direct reduction without extensive decomposition. Therefore, an alternative approach to the synthesis of F-ring saturated analogs was developed. The EF heterocyclic moiety of the target structure 25 could be prepared via nitrenium ion mediated bicyclization of 26 (Scheme 6), an approach which should be feasible based upon studies presented in the art. However, a more incremental approach to the synthesis of the EF heterobicyclic ring system was developed via iodoetherification of 28 to give 27, which on treatment with ammonia would generate the requisite EF heterobicyclic ring system (Scheme 6).

SCHEME 6

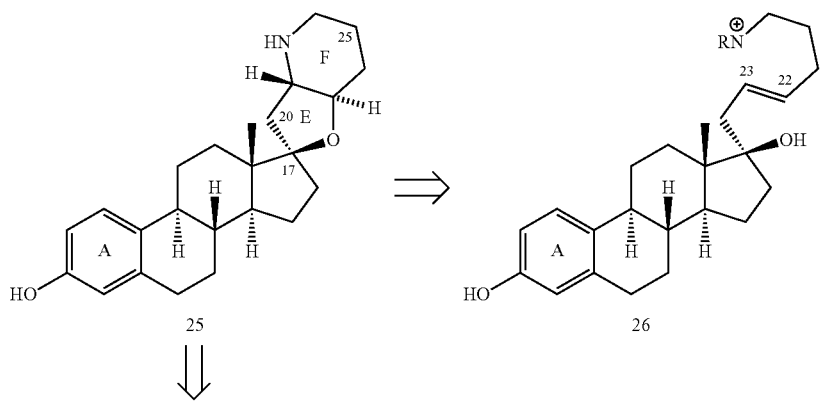

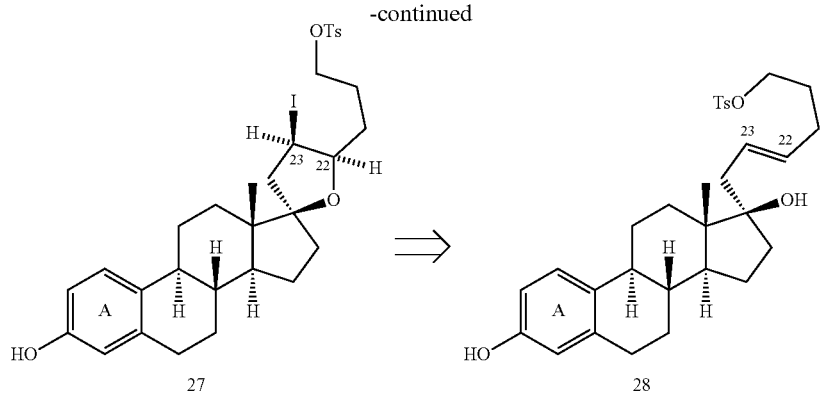

The synthesis and reaction of the key iodoetherification substrate 31 is outlined in Scheme 7.

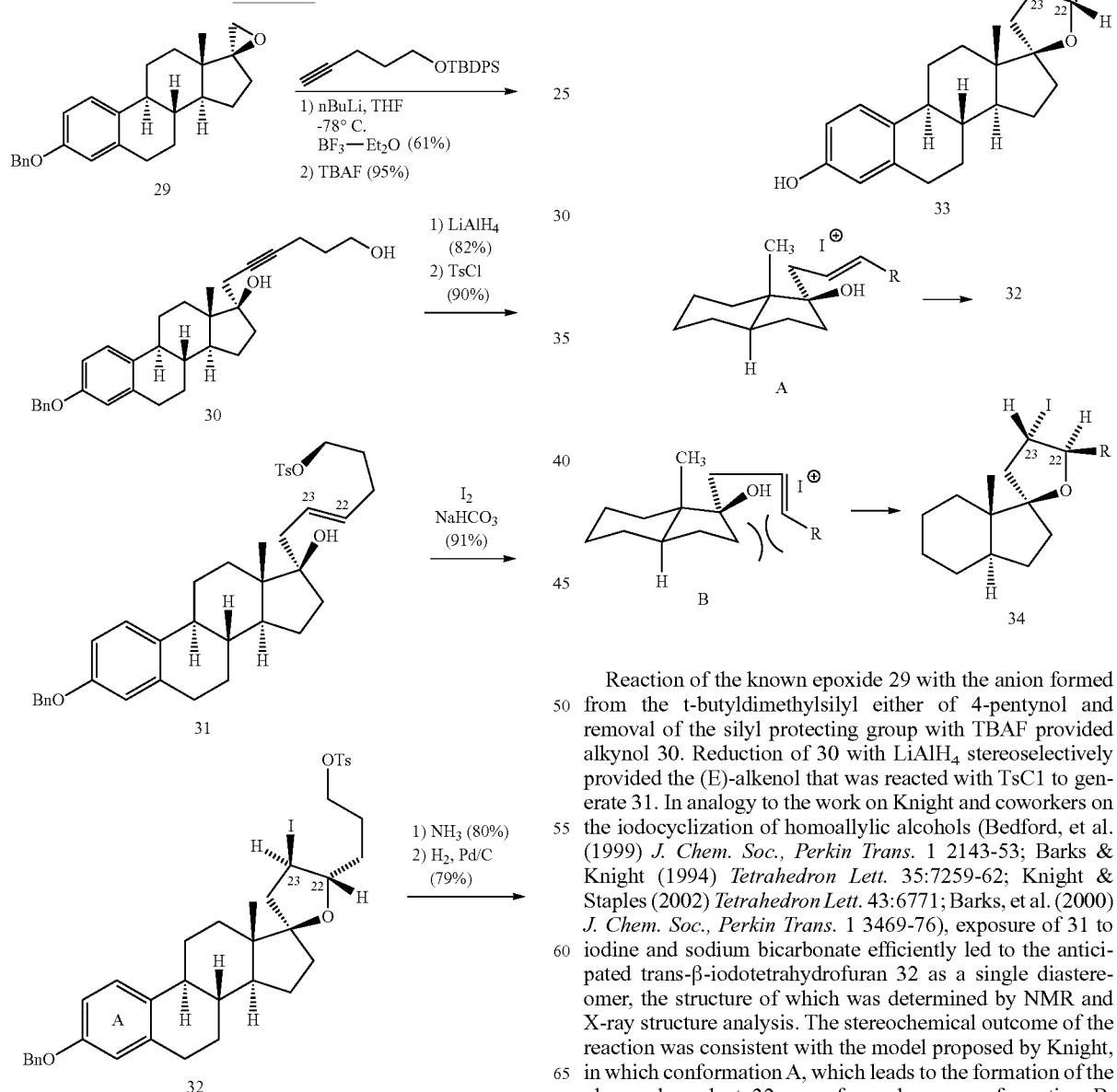

Reaction of the known epoxide 29 with the anion formed from the t-butyldimethylsilyl ether of 4-pentynol and removal of the silyl protecting group with TBAF provided alkynol 30. Reduction of 30 with $LiAlH_4$ stereoselectively provided the (E)-alkenol that was reacted with TsCl to generate 31. In analogy to the work on Knight and coworkers on the iodocyclization of homoallylic alcohols (Bedford, et al. (1999) *J. Chem. Soc., Perkin Trans.* 1 2143-53; Barks & Knight (1994) *Tetrahedron Lett.* 35:7259-62; Knight & Staples (2002) *Tetrahedron Lett.* 43:6771; Barks, et al. (2000) *J. Chem. Soc., Perkin Trans.* 1 3469-76), exposure of 31 to iodine and sodium bicarbonate efficiently led to the anticipated trans-β-iodotetrahydrofuran 32 as a single diastereomer, the structure of which was determined by NMR and X-ray structure analysis. The stereochemical outcome of the reaction was consistent with the model proposed by Knight, in which conformation A, which leads to the formation of the observed product 32, was favored over conformation B, which would lead to the formation of the diastereomeric trans-disubstituted tetrahydrofuran 34, in which only the hydrindane moiety of the estrone framework is shown.

Reaction of 32 with liquid ammonia afforded a piperidine product via displacement of both the iodide and tosylate moieties present in 31, followed by reductive debenzylation to generate 33, which was epimeric with the target structure of analog 25 at C-22, i.e., cis-instead of trans-EF ring fusion stereochemistry (nine chemical steps and 23% overall yield from estrone).

Example 4

Synthesis of Analogs Lacking E-Ring Tetrahydrofuran

Although the work of Knight (Bedford, et al. (1999) supra; Barks & Knight (1994) supra; Knight & Staples (2002) supra; Barks, et al. (2000) supra) had demonstrated that the iodoetherification of Z-homoallylic alcohols was slower than that of the E-alkene substrates, it was envisioned that the trans EF ring fusion stereochemistry found in cyclopamine and in analog 25 could result from analogous reaction of 35, the Z-alkene corresponding to 31, the synthesis of which is outlined in Scheme 8. In the event, Lindlar reduction of 30 afforded 35, which on exposure to iodine-mediated cyclization conditions afforded not the anticipated tetrahydrofuran product analogous to 32 (Scheme 7) but instead the oxetane 36 in 91% yield. Reaction of bis-electrophile 36 with ammonia afforded the oxetane-pyrrolidine 37 in 55% overall yield after O-debenzylation. The stereochemistry of 37 was unequivocally established by X-ray crystallographic analysis, confirming that the cyclization occurred with the analogous orientation of the Z-alkene (A' in Scheme 8) as shown in A (Scheme 7) for the E-alkene cyclization substrate 31. However, instead of the anticipated tetrahydrofuran product (the result of 5-endo cyclization), based on the work of Knight, the exclusive formation of the oxetane product 37 was observed, the result of 4-exo cycliztion of 35.

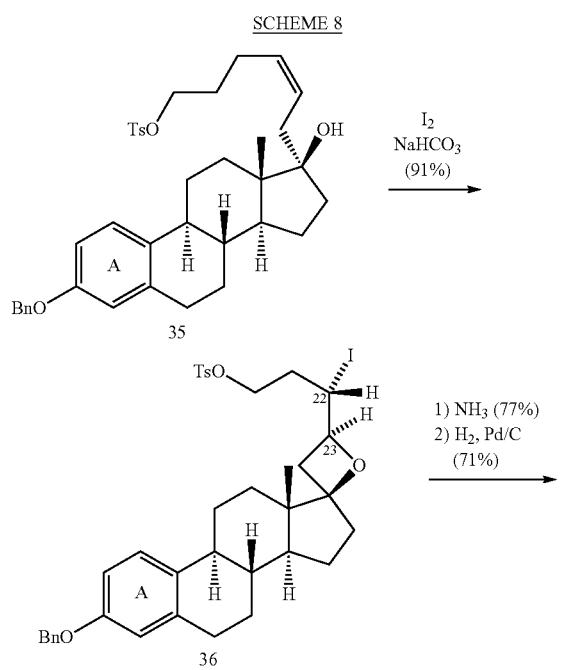

SCHEME 8

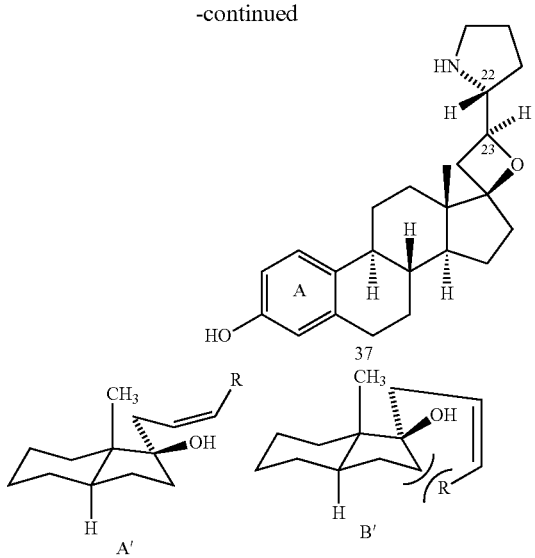

Example 5

Biological Activity of Analogs

The activity of analogs 33 and 37 on the SHH signaling pathway was analyzed using the SHH-Light2 cells described herein. Treatment of these cells with recombinant SHH activates GLI-dependent firefly luciferase expression and this SHH-induced activation is inhibited when cells are also treated with cyclopamine. In this assay, analogs 33 and 37 both lead to a strong inhibition of SHH signaling activity comparable to that of cyclopamine (FIG. 4).

To test whether analogs 33 and 37 also acted as SHH inhibitors in another biological system, cerebellar GNPs were analyzed. SHH is a potent mitogen for postnatal mouse cerebellar GNPs. GNPs represent a physiological system to test for the activity of analogs 33 and 37 as compared to cyclopamine, which blocks their proliferation.

GNPs were purified from postnatal day 5 (P5) mouse cerebella and treated with either SHH alone, or SHH in combination with cyclopamine, analog 33, or analog 37, each used at 5 mM. BrdU was added to the media 6 hours before fixation. Percentage of brdU positive was determined following counting with a fluorescence microscope using a 20× objective (AXIOSKOP, ZEISS). At least five independent fields for each culture condition were counted. The analysis was performed on three independent experiments. Statistical analysis was performed with the Student t test. As shown in FIG. 5, GNP proliferation in response to SHH signalling activation was blocked with cyclopamine as well as with analogs 33 and 37.

Figure 6:
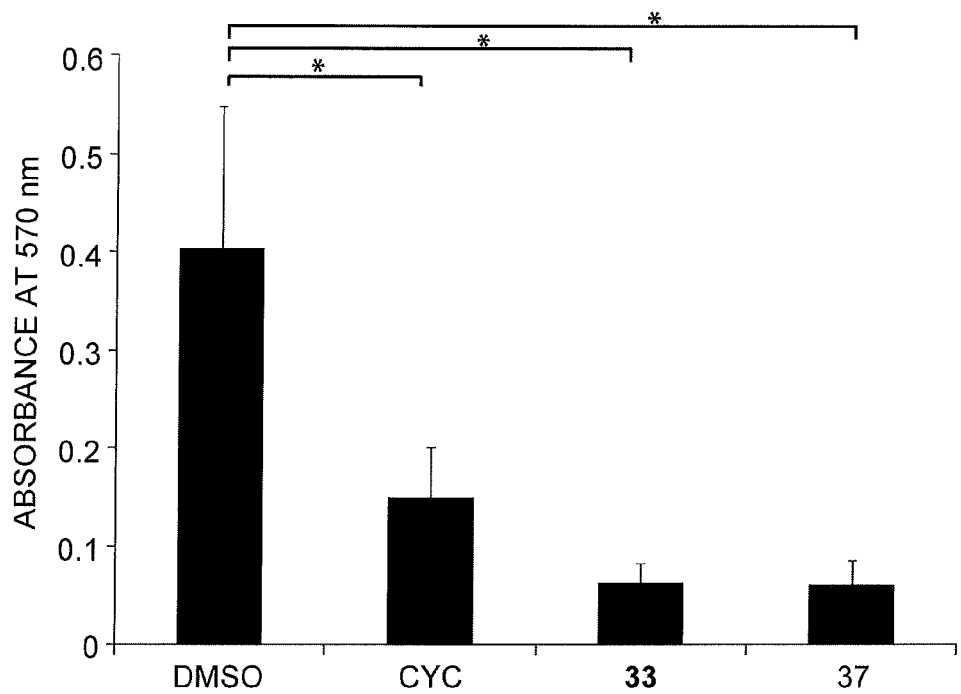
FIG. 6 shows the effect of analogs 33 and 37 on cell survival of human medulloblastoma DAOY cells. DAOY cells were treated for 72 hours with either cyclopamine (CYC), analog 33 or analog 37 before cell survival was assayed with a colorimetric MTT assay. Absorbance at 570 nm is directly proportional to the number of living cells. Note the significant decrease of cell survival when the cells were treated with CYC, analog 33 or analog 37 (Asterisk indicates p-value $p<0.05$).

Abnormal activation of the SHH signaling pathway has been linked to various cancers including medulloblastoma, a malignancy of the cerebellum with the highest incidence of all human pediatric malignant brain tumors. A subset of these tumors is thought to arise from deregulation of GNP development in the cerebellum and require SHH signaling for their growth. It was therefore tested whether analogs 33 and 37 were also efficient in reducing the viability of medulloblastoma cells using human medulloblastoma DAOY cells. The results presented in FIG. 6 show that both analogs 33 and 37 were active in reducing DAOY cells viability.

Overall, the results of the biological evaluation of analogs 33 and 37 indicate that both analogs are highly potent inhibitors of Hedgehog signaling, comparable to cyclopamine in potency. Moreover, based upon the results observed for analog 37, the tetrahydrofuran E ring of cyclopamine does not appear to be required for biological function.

What is claimed is:

1. A steroid-derived cyclopamine analog that inhibits sonic hedgehog signaling, wherein said analog has the structure:

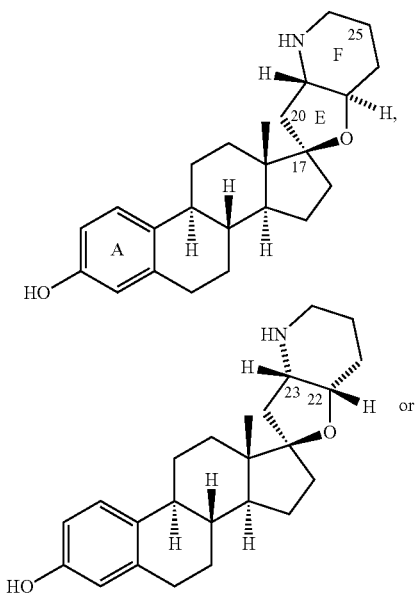

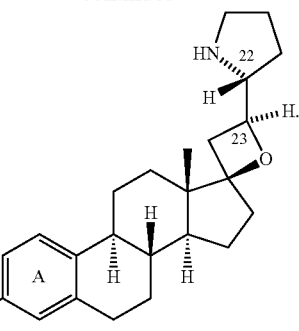

2. A pharmaceutical composition comprising a steroid-derived cyclopamine analog of claim 1 in admixture with a pharmaceutically acceptable carrier.

3. The pharmaceutical composition of claim 2, wherein said composition is formulated for parenteral, transdermal, oral, subcutaneous, intrapulmonary, topical or intranasal administration.

4. A method for inhibiting sonic hedgehog signaling in a cell comprising contacting a cell with steroid-derived cyclopamine analog of claim 1 thereby inhibiting sonic hedgehog signaling in the cell.

5. The method of claim 4, wherein said method is carried out in vitro.

6. The method of claim 4, wherein the cell is a cancer cell.

* * * * *